(12) United States Patent
Crandall et al.

(10) Patent No.: US 7,322,979 B2
(45) Date of Patent: Jan. 29, 2008

(54) MULTIDIRECTIONAL PIVOTING BONE SCREW AND FIXATION SYSTEM

(75) Inventors: Dennis Crandall, Mesa, AZ (US); Matthew M. Morrison, Cordova, TN (US); Terrance Strohkirch, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 10/291,946

(22) Filed: Nov. 11, 2002

(65) Prior Publication Data

US 2003/0105460 A1    Jun. 5, 2003

Related U.S. Application Data

(63) Continuation-in-part of application No. 09/941,153, filed on Aug. 28, 2001, now abandoned, which is a continuation of application No. 09/526,435, filed on Mar. 15, 2000, now Pat. No. 6,309,391.

(51) Int. Cl.
*A61B 17/56* (2006.01)

(52) U.S. Cl. ...................................... 606/61

(58) Field of Classification Search .................. 606/61, 606/73, 72, 60
See application file for complete search history.

(56) References Cited

U.S. PATENT DOCUMENTS

| | | | |
|---|---|---|---|
| 2,696,817 A * | 12/1954 | Prevo | 623/20.12 |
| 3,991,425 A * | 11/1976 | Martin et al. | 623/18.11 |
| 5,002,542 A | 3/1991 | Frigg | |
| 5,196,013 A | 3/1993 | Harms et al. | |
| 5,499,983 A * | 3/1996 | Hughes | 606/61 |
| 5,545,166 A | 8/1996 | Howland | |
| 5,569,247 A | 10/1996 | Morrison | |
| 5,591,166 A | 1/1997 | Bernhardt et al. | |
| 5,628,740 A | 5/1997 | Mullane | |
| 5,643,263 A | 7/1997 | Simonson | |
| 5,649,926 A | 7/1997 | Howland | |
| 5,752,957 A | 5/1998 | Ralph et al. | |
| 5,766,254 A | 6/1998 | Gelbard | |
| 5,800,435 A | 9/1998 | Errico et al. | |
| 5,810,819 A | 9/1998 | Errico et al. | |
| 5,814,046 A * | 9/1998 | Hopf | 606/61 |
| 5,885,285 A | 3/1999 | Simonson | |

(Continued)

*Primary Examiner*—Melba N. Bumgarner
(74) *Attorney, Agent, or Firm*—Woodard, Emhardt, Moriarty, McNett & Henry LLP

(57) ABSTRACT

A double-jointed bone bolt for use in an apparatus for maintaining vertebra in a desired relationship. The apparatus has a rod that extends substantially along the spine and one or more bone bolts. At least one of the bone bolts is double jointed. The double-jointed bolt has a mounting portion with a hook or coarse threads to engage a vertebra, and the mounting portion is attached to a pivot post in a manner that allows the pivot post to be rotatable about a common axis in respect to the mounting portion. The pivot post of the bone bolt is then pivotally attached to a connector portion of the bone bolt that has machine threads upon which a surgeon may attach a clamp. The clamp has a second bolt and an arm. The second bolt holds the rod and the arm to the clamp. The second bolt has a first channel to attach to the rod, while the arm has a second channel to attach the double-jointed bone bolt.

9 Claims, 15 Drawing Sheets

U.S. PATENT DOCUMENTS

| | | |
|---|---|---|
| 5,938,663 A | 8/1999 | Petreto |
| 5,976,135 A | 11/1999 | Sherman |
| 5,983,521 A | 11/1999 | Montague et al. |
| 5,989,250 A | 11/1999 | Wagner et al. |
| 6,017,344 A | 1/2000 | Errico et al. |
| 6,183,473 B1 | 2/2001 | Ashman |
| 6,187,005 B1 | 2/2001 | Brace et al. |
| 6,248,107 B1 | 6/2001 | Foley et al. |
| 6,309,391 B1 | 10/2001 | Crandall et al. |
| 6,478,798 B1 * | 11/2002 | Howland .................... 606/61 |
| 2002/0058942 A1 * | 5/2002 | Biedermann et al. ......... 606/73 |
| 2003/0176861 A1 * | 9/2003 | Reed .......................... 606/61 |

* cited by examiner

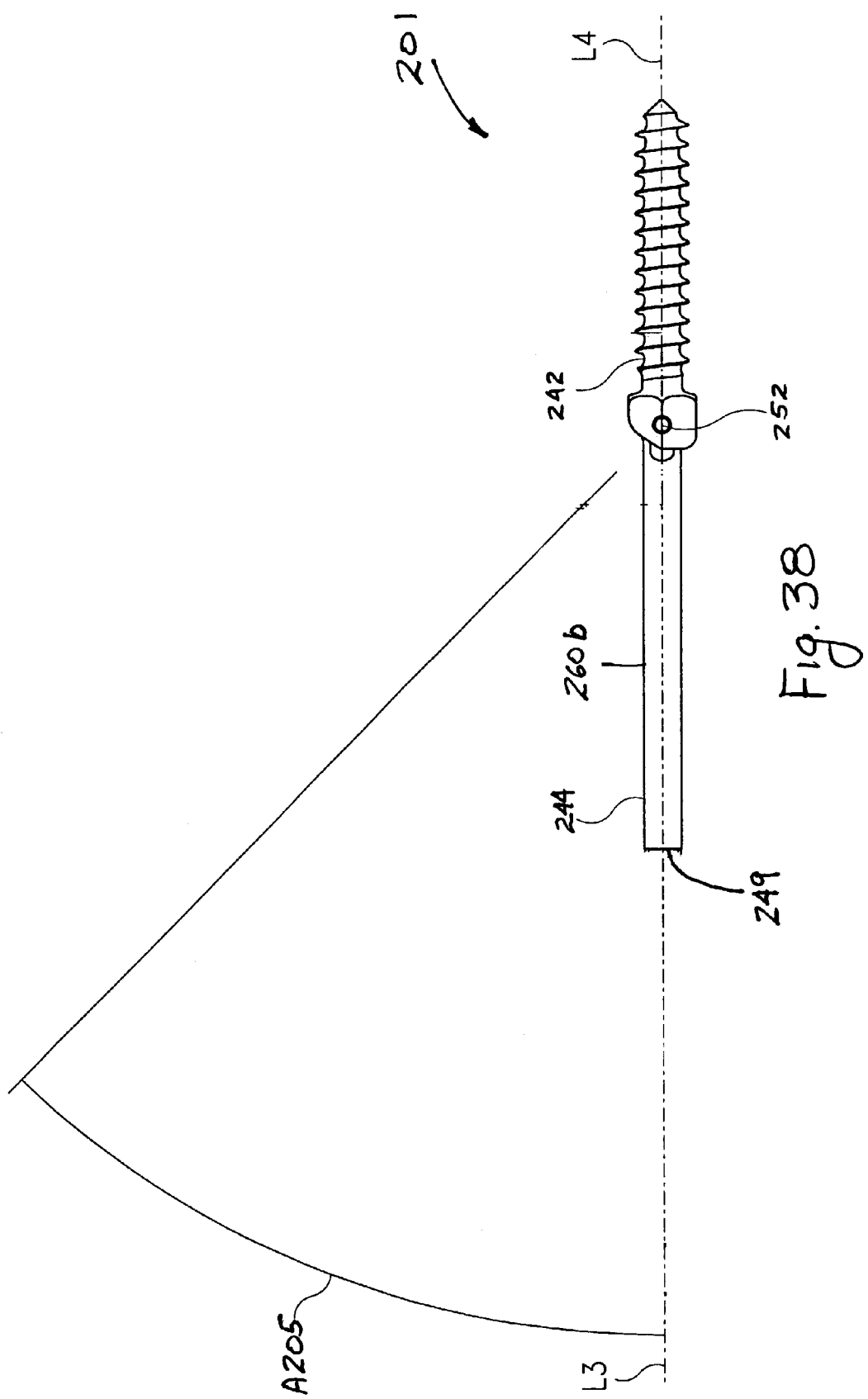

MULTIDIRECTIONAL PIVOTING BONE SCREW AND FIXATION SYSTEM

CROSS REFERENCE TO RELATED APPLICATIONS

This application is a continuation in part of and claims priority to U.S. patent application Ser. No. 09/941,153, filed Aug. 28, 2001 now abandoned which is a continuation of U.S. patent application Ser. No. 09/526,435, filed Mar. 15, 2000, now issued as U.S. Pat. No. 6,309,391, which is incorporated herein by reference.

FIELD OF THE INVENTION

This invention relates to orthopedics and spinal surgery, and more particularly relates to a double-hinged bone screw to accommodate the differences in position of adjacent bolts implanted in adjacent vertebrae, which bolts are all mounted to a common spinal rod.

BACKGROUND

Spinal implant systems provide a rod for supporting the spine and properly positioning components of the spine for various treatment purposes. Bolts or screws are typically secured into the vertebrae for connection to a supporting rod. These bolts must frequently be positioned at various angles due to the anatomical structure of the patient, the physiological problem to be treated, and the preference of the physician. It is difficult to provide secure connection between the spinal support rod and these connecting bolts at various angles, and where there are differing distances between the rod and bolts and different heights relative to these components.

SUMMARY OF THE INVENTION

In one aspect, this invention is a bolt for connecting a vertebra to a longitudinal member. The bolt has a mounting portion with a hook or coarse threads to engage a vertebra. The mounting portion is attached to a pivot post in a manner that allows the pivot post to be rotatable about a common axis in respect to the mounting portion of the bolt. The pivot post is then pivotally attached to a connector portion that has machine threads upon which a surgeon may attach other structures.

In another aspect, this invention is an apparatus for maintaining vertebra in a desired relationship. The apparatus has a rod that extends substantially along the spine and one or more bone bolts. At least one of the bone bolt has a mounting portion with a hook or coarse threads to engage a vertebra, and the mounting portion is attached to a pivot post in a manner that allows the pivot post to be rotatable about a common axis in respect to the mounting portion of the bolt. The pivot post of the bone bolt is then pivotally attached to a connector portion of the bone bolt that has machine threads upon which a surgeon attaches a clamp. The clamp, also a part of this embodiment of the invention, has a second bolt and an arm. The second bolt holds the rod and the arm to the clamp. The second bolt has a first channel to hold the rod while the arm has a second channel to hold the bone bolt.

It is an object of this invention to provide a connection assembly that will allow connection between a spinal support rod to a vertebra at a variety of angles relative to the vertical, taken when the patient is lying down.

BRIEF DESCRIPTION OF THE DRAWING

FIG. 38 is a side elevational view of a bone bolt according to another embodiment of the present invention.

DESCRIPTION OF THE PREFERRED EMBODIMENT

Specific language is used in the following description to publicly disclose the invention and to convey its principles to others. No limits on the breadth of the patent rights based simply on using specific language are intended. Also included are any alterations and modifications to the description that should normally occur to one of average skill in this technology.

This application incorporates by reference the following U.S. patent applications co-owned with the present application: Ser. No. 09/526,104, filed Mar. 15, 2002 for SPINAL IMPLANT CONNECTION ASSEMBLY; Ser. No. 09/694,703, filed Oct. 23, 2000 for SIX AXIS CONNECTOR FOR SPINAL FIXATION; Ser. No. 09/694,702, filed Oct. 23, 2000 for TAPER-LOCKED ADJUSTABLE CONNECTOR; and Ser. No. 09/694,291, filed Oct. 23, 2000 for SPINAL IMPLANT CONNECTION ASSEMBLY.

Figure 1:
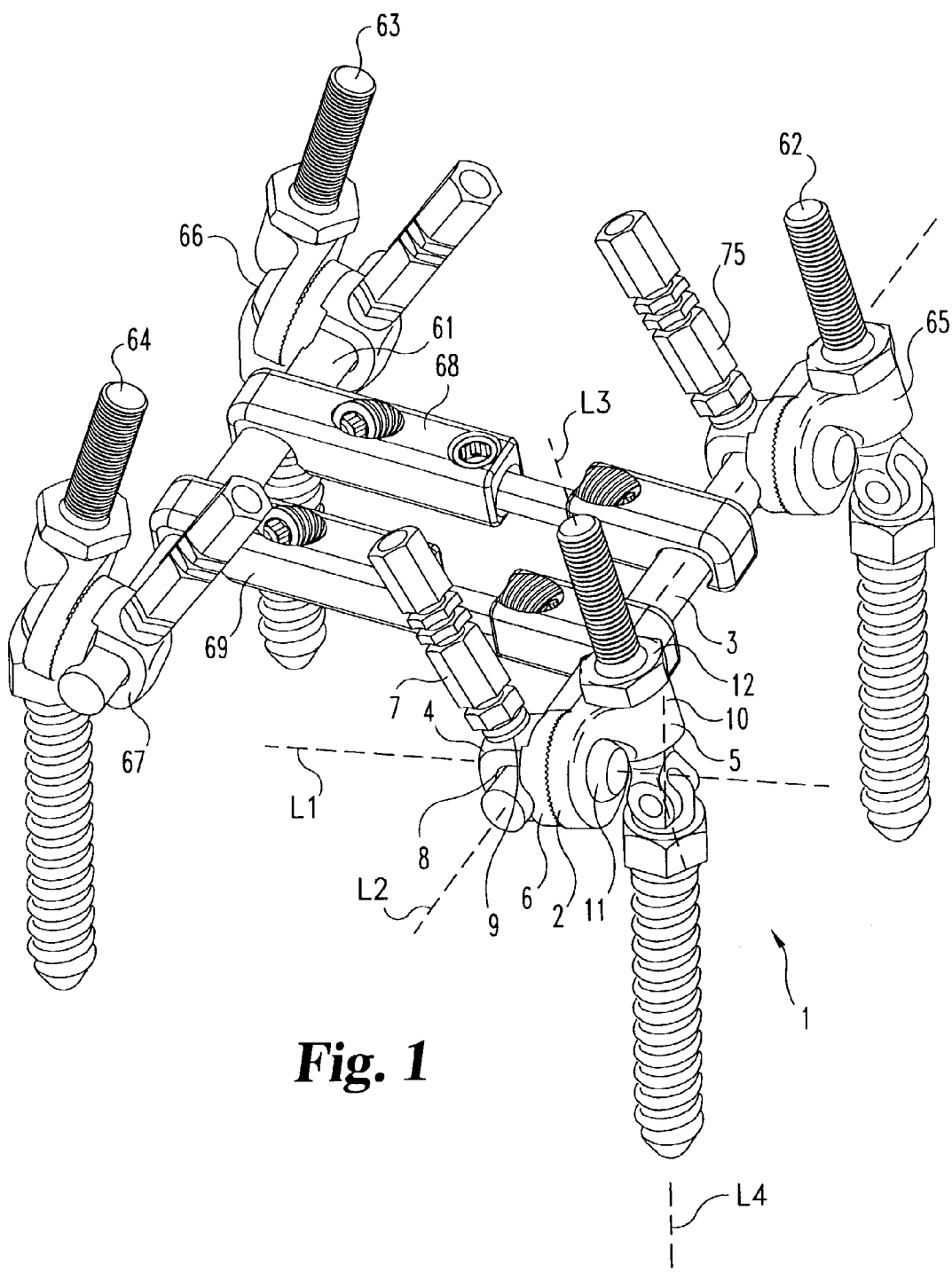
FIG. 1 is a perspective view of one embodiment of the present invention.

A bone bolt 1 according to one embodiment of the invention is shown as part of a larger spinal implant system in FIG. 1. Bone bolt 1 is shown attached to a clamp 2 with the longitudinal axis L1, and clamp 2 is shown attached to a spinal implant rod 3 with a longitudinal axis L2. Clamp 2 includes a clamp bolt 4, an arm 5, a rod interface washer 6, a set screw 7, and a nut 12. Clamp bolt 4 has an aperture 8 for receiving rod 3, and while the aperture is shown closed around rod 3, it will nevertheless be understood that an open-sided aperture may also be used to permit top-loading of rod 3 into clamp 2. Set screw 7 is inserted through a threaded opening 9 and into aperture 8 in clamp bolt 4 so as to allow set screw 7 to push against rod 3. Arm 5 has a bore 10 for receiving bone bolt 1. Arm 5 is simultaneously tightened to clamp 2 when set screw 7 is tightened against rod 3. As set screw 7 pushes against rod 3, rod 3 pushes against rod interface washer 6, which pinches arm 5 between rod interface washer 6 and stop 11. In this manner, set screw 7 acts as a compression member to tighten clamp 2 and achieve substantial fixation of arm 5 to rod 3.

Figure 9:
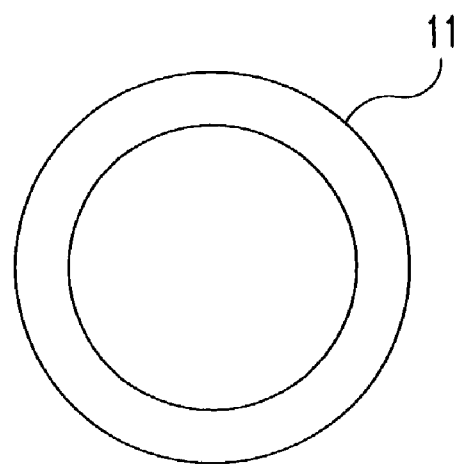
FIGS. 9-10 are respectively end and side views of a stop that may be used in one embodiment of the present invention.
Figure 10:
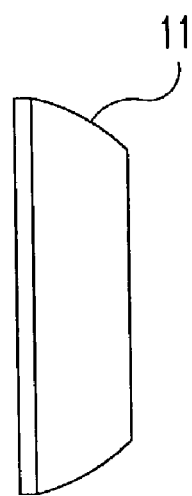
Figure 11:
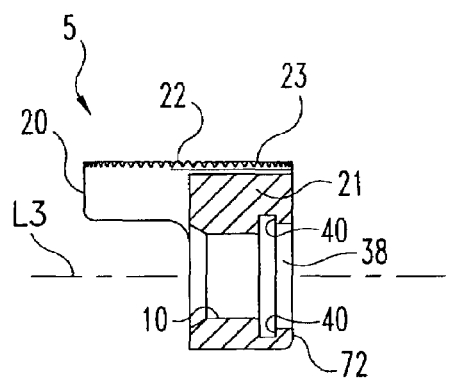
FIGS. 11-14 are respectively end cross-sectional, top, side, and side cross-sectional views of an arm that may be used in one embodiment of the present invention.

Details of clamp bolt 4 are shown in FIGS. 2-8. Clamp bolt 4 can be subdivided into bolt head portion 13, bolt shaft portion 14, washer seat portion 15 and washer stop portion 16. Threaded openings 9a & 9b, and aperture 8 reside in bolt head portion 13. Threaded openings 9a & 9b open into aperture 8 at an oblique angle A4 with respect to longitudinal axis L1 to allow set screw 7 (FIG. 1) to force spinal rod 3 toward the distal end 17 of aperture 8. Clamp bolt 4 is substantially symmetrical about longitudinal axis L1 such that threaded openings 9a and 9b are substantially mirror images. Bolt shaft portion 14 is generally cylindrical in shape and is sized to accept the eye 18 (FIGS. 13 & 14) of arm 5. Arm 5 is then held on shaft portion 14 by attaching stop 11 (shown in isolation in FIGS. 9 & 10) to the end 19 of shaft portion 14, either by welding or some other suitable means. As an alternative, shaft portion 14 may include threads and stop 11 may be correspondingly threaded onto shaft portion 14 to hold arm 5 in position. In this alternative design, stop 11 may be the compressive member utilized to tighten clamp 2 onto rod 3 instead a set screw threaded into bolt head portion 13.

Clamp bolt 4 also preferably includes washer seat portion 15 and washer stop portion 16. A washer seat portion 15 that is substantially rectangular in cross-section is currently preferred, but washer seat portion 15 can be of any suitable shape that may interlock with a complementary shape in rod interface washer 6 (FIGS. 1, 15, 16 & 17) to prevent rod interface washer 6 from rotating in relation to clamp bolt 4. As shown, a washer stop 16 is generally provided in clamp bolt 2 by placing a raised edge in bolt head portion 13. Washer stop 16 prevents rod interface washer 6 from being inadvertently removed from clamp 2.

Details of arm 5 are shown in FIGS. 11-14. Arm 5 includes a flange portion 20, and a collar portion 21. Flange portion 20 has an eye 18, and as previously presented, clamp bolt 4 attaches to arm 5 by placing the shaft portion 14 of clamp bolt 4 through eye 18 and then attaching stop 11 on end 19 of shaft portion 14. The medial face 22 of flange portion 20 also includes a connection surface 23. Connection surface 23 preferably includes structure for facilitating the engagement of arm 5 against rotational movement relative to rod interface washer 6. This engagement structure is preferably a plurality of variable angle ridges that radiate from the rotational center of eye 18. In other words, the structure is a set of interlocking teeth that can generally be characterized as male protrusions and complementary female cavities that upon interlock, prevent rod interface washer 6 from rotating in respect to arm 5.

Figure 12:
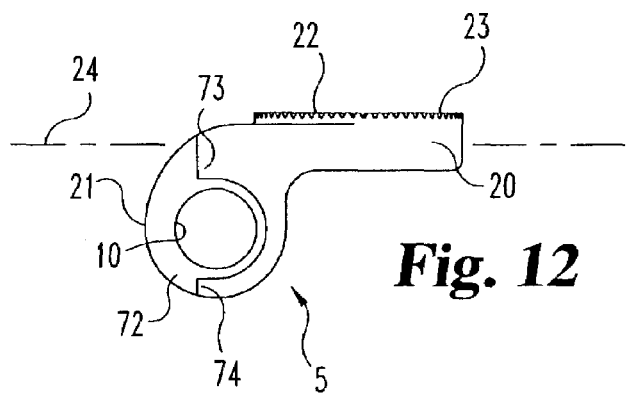
Figure 18:
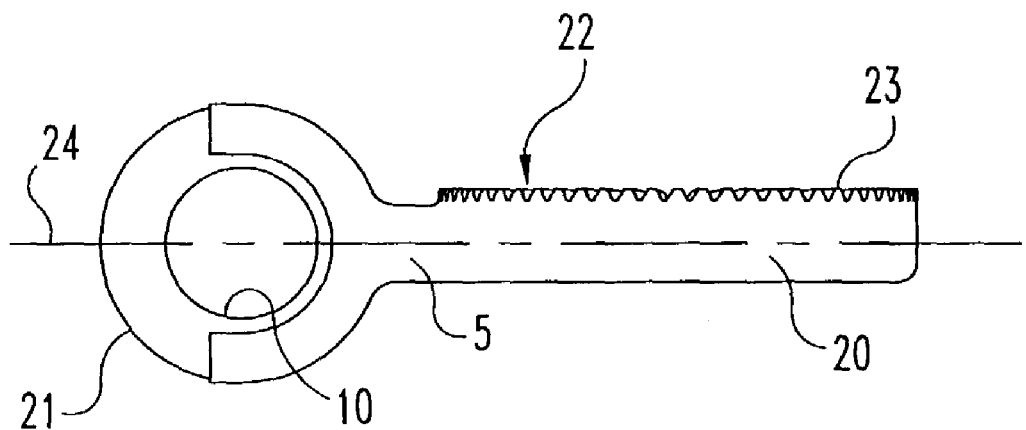
FIGS. 18, 19 are top views of alternative embodiments for an arm in the practice of the present invention.
Figure 19:
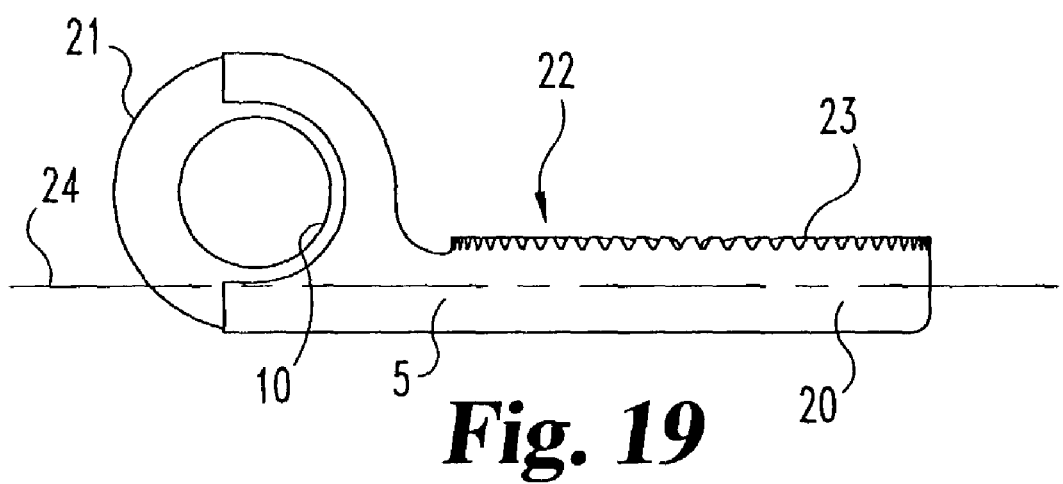

Referring to FIGS. 12, 18 and 19; collar portion 21 of arm 5 has a bore 10. Bore 10 may assume various orientations in relation to the centerline 24 of arm 5. FIG. 12 depicts bore 10 offset from centerline 24 toward the stop (not shown) of clamp bolt 4. Optionally, bore 10 can be offset from centerline 24 toward the clamp aperture 8 (not shown) of clamp bolt 4, as shown in FIG. 19, or bore 10 can be placed in the same plane as centerline 24, as shown in FIG. 18. It being understood that the alternative arm designs may permit even a smaller total width of clamp 2 by bringing bone bolt 1 closer to the rod 3.

Figure 20:
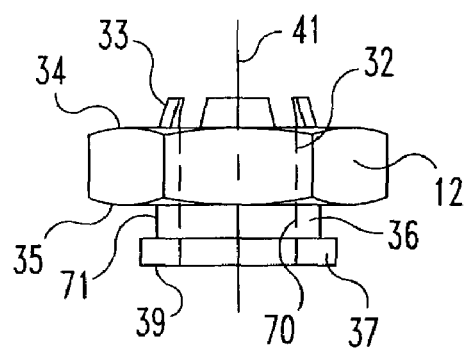
FIG. 20 is a side view of a nut that may be used in one embodiment of the present invention.

Referring to FIG. 20, there is shown nut 12, which is preferably used to threadably engage bone bolt 1 (not shown) to arm 5, and prevent bone bolt 1 from moving longitudinally along longitudinal axis L3 with respect to arm 5. Nut 12 has as set of internal threads 32 to mate with the machine threads 60 on bone bolt 1 and a set of locking tabs 33 on the proximal face 34 of nut 12 to firmly hold nut 12 upon bone bolt 1 once nut 12 is threaded into place. The distal face 35 of nut 12 also includes an annular collar 36. Annular collar 36 is integrally connected to nut 12, and has a channel 70 that opens into internal threads 32. The end 39 of collar 36 terminates in an annular rim 37 that laterally projects beyond the diameter of annular collar 36, and forms an annular groove 71 between annular rim 37 and distal face 35 of nut 12.

Referring back to FIGS. 11-14, arm 5 is preferably adapted to rotatably secure nut 12 by annular rim 37 and annular collar 36. The proximal face 72 of collar portion 21 of arm 5 includes a semicircular cavity 38 around the entrance of bore 10 that is sized to accept annular collar 36 and annular rim 37. By fitting collar 36 and rim 37 into cavity 38, annular rim 37 rides against semi-circular lip 40, on the roof of cavity 38; opening 70 and internal threads 32 of nut 12 are axially aligned with bore 10 of arm 5; and nut 12 is rotatably secured to arm 5. In other words, nut 12 is free to rotate about axis 41 or axis L3, but nut 12 is substantially fixed against movement along longitudinal axis L3 (FIGS. 11 & 13) relative to arm 5 because annular rim 37 rides against semi-circular lip 40 in one direction and proximal face 72 in the other. In one preferred embodiment, nut 12 is temporarily held in semicircular cavity 38 by slightly bending corners 73 & 74 of lip 40 against annular rim 37. Bending these corners will temporarily hold nut 12 in arm 5 until the surgeon threads nut 12 onto bone bolt 1, and will not significantly hinder the surgeon's rotation of nut 12 around bone bolt 1.

Figure 15:
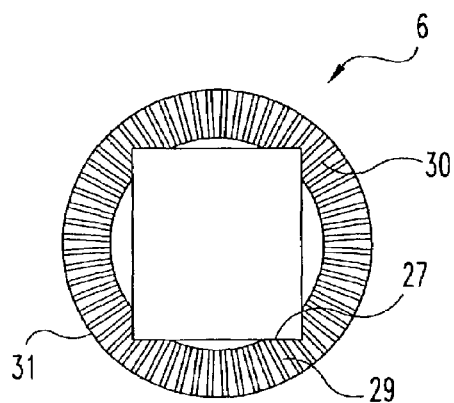
FIGS. 15-17 are respectively end, side, and top views of a washer that may be used in one embodiment of the present invention.
Figure 16:
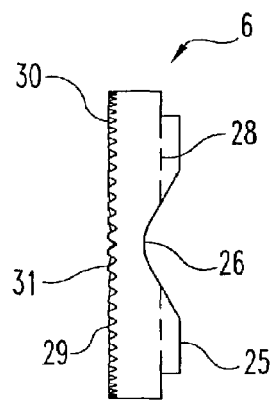
Figure 17:
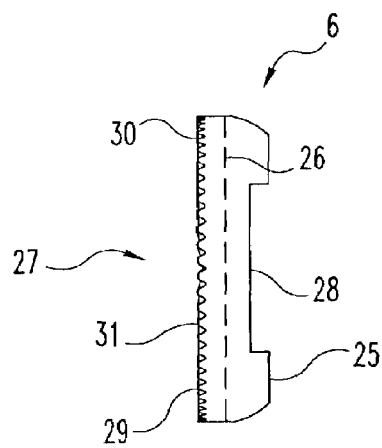

Details of rod interface washer 6 are shown in FIGS. 15, 16 & 17. Rod interface washer 6 can be any of several suitable shapes, including the circle that is depicted. The medial face 25 of the rod interface washer 6 has an engagement surface, which preferably includes an engagement groove 26 that accepts a cylindrical spinal implant rod (such as rod 3 in FIG. 1). Engagement groove 26 preferably runs across the entire face of medial face 25. Rod interface washer 6 also has a central opening 27 that corresponds to the cross-sectional shape of previously presented washer seat portion 15 in clamp bolt 4. In the currently preferred embodiment, both washer seat portion 15 and opening 27 are substantially square. Although, this shape could vary from many possible shapes that would similarly prevent rod interface washer 6 from rotating in respect to clamp bolt 4. To assist in this regard, it is also preferable that rod interface washer have a guide groove 28 to accept bolt head portion 13 of clamp bolt 4 to further lock clamp bolt 4 and rod interface washer 6 together. It should be noted that guide groove 28 and engagement groove 26 are preferably placed in such a manner that orients aperture 8 substantially parallel to groove 26. This placement helps insure that spinal rod 3 will be held in the connector assembly in a direction that is substantially perpendicular to clamp bolt 4, and in turn, also substantially perpendicular to set screw 7.

Figure 13:
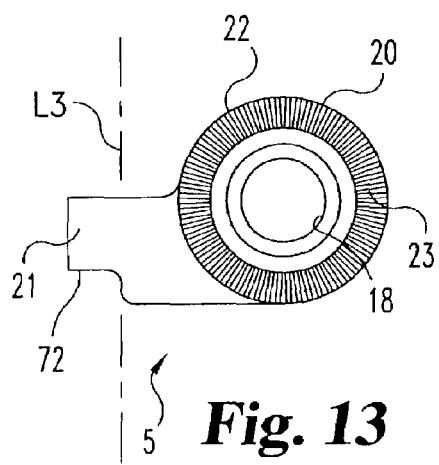
Figure 14:
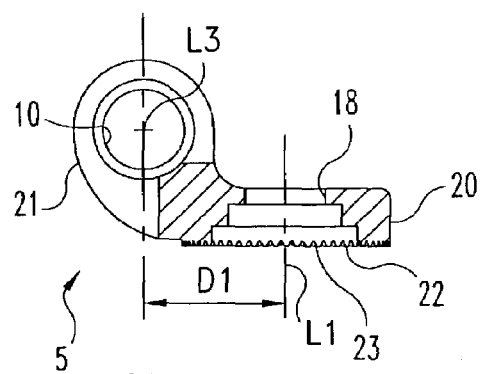

Rod interface washer 4 also includes connection surface 29 on the lateral face 30 of rod interface washer 6. Connection surface 29 preferably includes structure for facilitating the engagement of rod interface washer 6 against rotational movement relative to arm 5. This engagement structure is preferably a plurality of variable angle ridges 31 that radiate from the rotational center of rod engagement washer 6, similar to those previously described on the medial face 22 on flange 20 of arm 5. Variable angle ridges 31 are sized to mate with the similar variable angle ridges 23 on arm 5. Referring to FIGS. 13 and 15, both sets of ridges consist of alternating male protrusions and female cavities. Hence, once placed together, these interlocking ridges prevent rod engagement washer 6 from rotating in respect to arm 5. And although radiating ridges are shown to facilitate the fixation of these two parts, it is also contemplated that other structures could serve this function. For example, it is also contemplated that one could use any number of interlocking male and female structures such as rounded bumps or knurling and mating cavities. The locking engagement of connection surface 23 with connection surface 29 may occur at any of a plurality of angles. More specifically, the angle between longitudinal axis L3 of bone bolt 1 and the longitudinal axis L2 of rod 3 may be adjusted to meet the requirements of the patient's anatomy.

Figure 25:
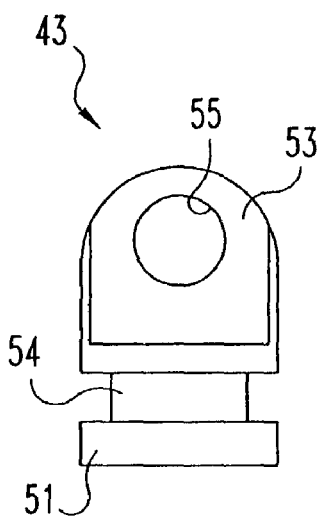
FIGS. 25 and 26 are respectively front and side views of a pivot post in a bone bolt according to one embodiment of the present invention.
Figure 26:
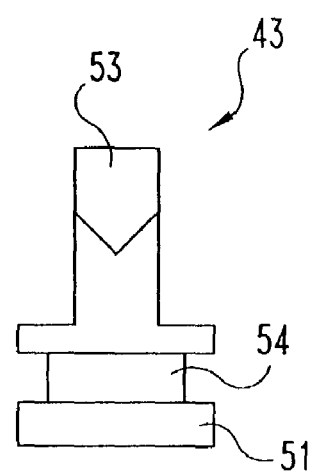
Figure 27:
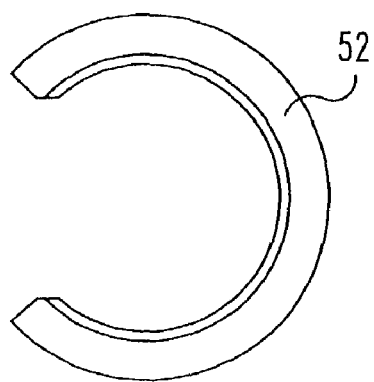
FIG. 27 is a top view of a snap ring for a bone bolt according to one embodiment of the present invention.

Details of bone bolt 1 can be seen in FIGS. 21-28. Bone bolt 1 includes a mounting portion 42, a pivot post 43, and a connector portion 44. The distal end of mounting portion 42 has a set of coarse threads 45. Coarse threads 45 have a thread convolution for engaging cancellous bone and terminate in a tapered tip 46. Tapered tip 46 helps align bone bolt 1 into a predrilled opening in a vertebra and also helps coarse threads 45 to gradually engage and advance into the vertebra upon rotation of mounting portion 21. In this regard, although coarse threads are shown as a means for engaging a vertebra, it is also contemplated that a hook, mounted on the end of mounting portion 42, could also be used as an alternative means to engage a vertebra. The proximal end 47 of mounting portion 42 terminates in hex-headed drive portion 49. The inside of hex-headed drive portion 49 includes an annular receptacle 48, and the inner wall of receptacle 48 has an annular groove 50. (FIG. 22) Annular receptacle 48 is sized to accept hub 51 of pivot post 43 (FIGS. 25 & 26), and annular groove 50 is sized to accept snap ring 52. (FIG. 27)

Pivot post 43 is shown in isolation in FIGS. 25 & 26. Pivot post 43 has a hub 51 and an ear 53 with a channel 55. Hub 51 preferably has a circular cross-section and is circumscribed by an annular groove 54. Hub 51 is sized to freely rotate about longitudinal axis L4 inside receptacle 48 of the mounting portion 42 of bone bolt 1. During assembly in one preferred embodiment, snap ring 52 (FIG. 27) is placed partly inside annular groove 54 before hub 51 is inserted into receptacle 48. Then, upon insertion into receptacle 48, snap ring 52 partially expands into annular groove 50, and thereby rotatably connects pivot post 53 to the proximal end 47 of mounting portion 42.

Figure 21:
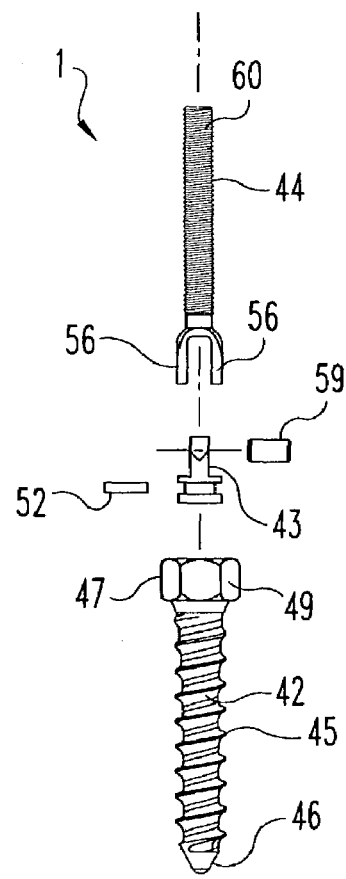
FIG. 21 is an exploded view of a bone bolt in one embodiment of the present invention.
Figure 22:
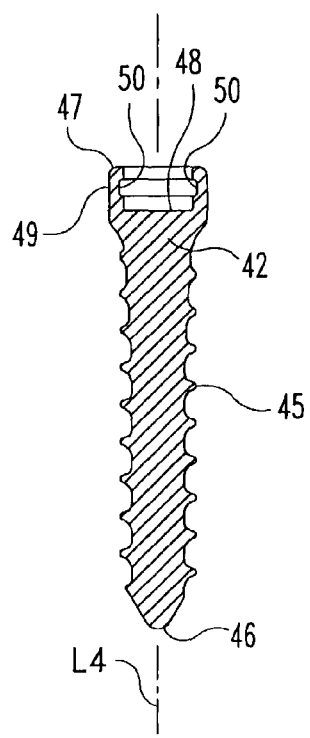
FIG. 22 is a cross-sectional view of a mounting portion of a bone bolt according to one embodiment of the present invention.
Figure 23:
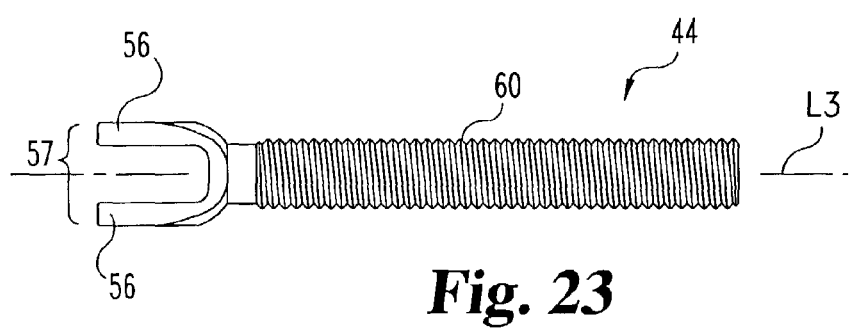
FIGS. 23 and 24 are respectively side and top views of a connecting portion of a bone bolt according to one embodiment of the present invention.
Figure 24:
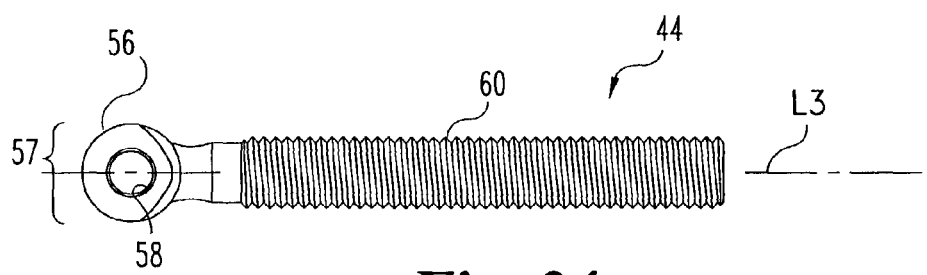
Figure 28:
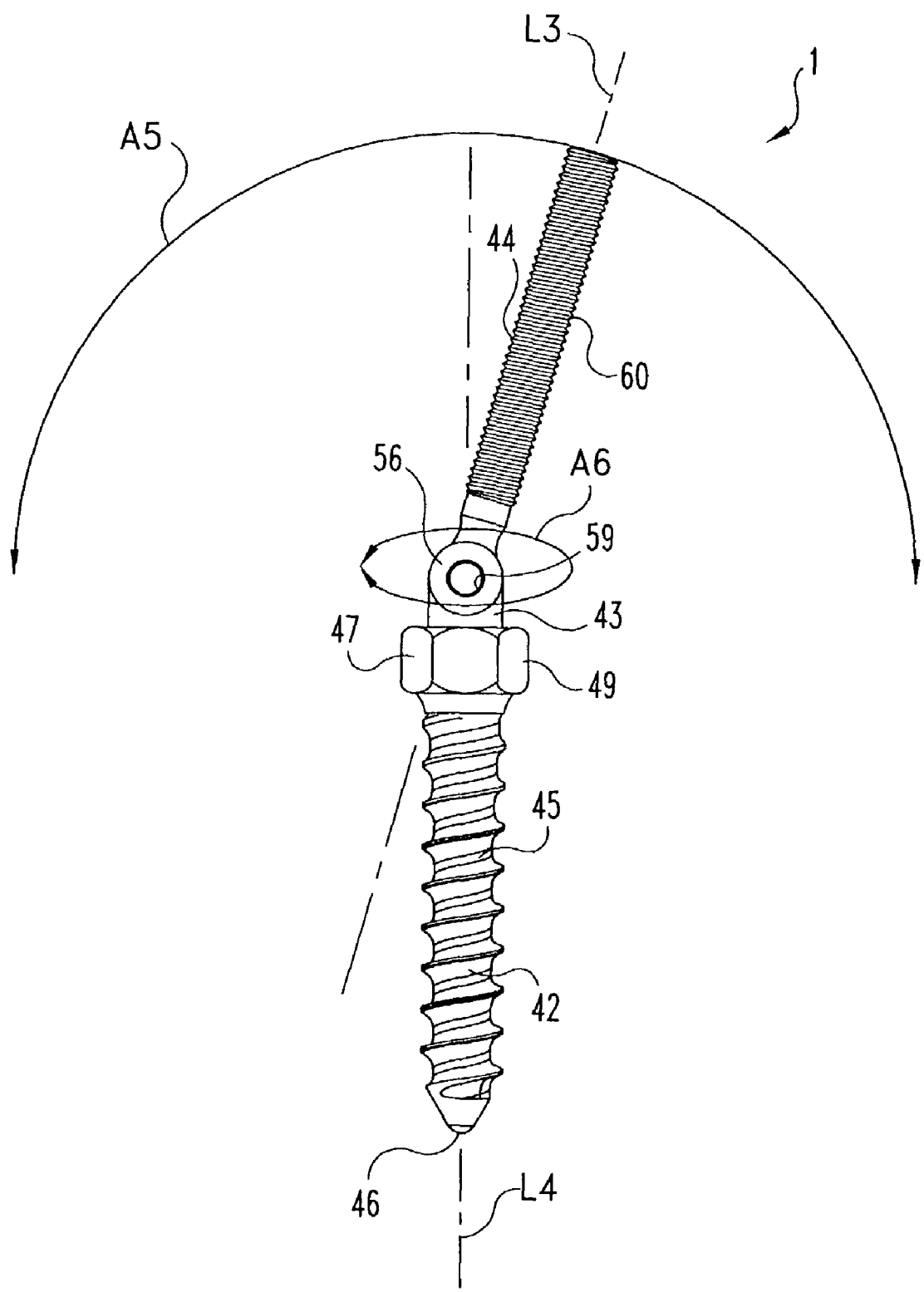
FIG. 28 is a side view of a bone bolt according to one embodiment of the present invention.

A top and side view of the connector portion 44 of bone bolt 1 is shown in FIGS. 23 & 24. Most of the longitudinal length of connector portion 44 is circumscribed with machine threads 60. The lower end 57 of connector portion 44 terminates with a pair of ears 56 that are diametrically opposite of each other at the radial perimeter of end 57. Each of the ears 56 includes an aperture or channel 58 for insertion of pin 59 (FIG. 21). During assembly, pin 59 is inserted through aperture 58 in one ear, then through channel 55 in pivot post 43, and then through aperture 58 in the other ear. Thusly joined to mounting portion 42 and pivot post 43, the connector portion 44 of bolt 1 may be pivoted around pin 59 as depicted by arc A5, and may also be rotated around longitudinal axis L4 of the mounting portion 42, as depicted by arc A6. (FIG. 28)

Referring back to FIG. 1, a typical construct in the use of this invention typically has two or more largely identical rods, 3 and 61, and at least two or more bone bolts 1, 62-64 attached to each rod by clamps 2, 65-67. And optionally, the rods may be joined by one or more cross-linking members 68 & 69. An example of a suitable cross-linking member is described in U.S. Pat. No. 5,947,966 to Drewry et al, the disclosure of which is specifically incorporated into this specification by reference. And although each of the clamps and bone bolts shown in this figure are identical, it is further contemplated that other clamps and bone bolts could be incorporated in a common construct in the use of this invention. For example, one could also use the clamps and bone bolts described in U.S. Pat. Nos. 5,643,263 and 5,885,285 to Simonson, the disclosures of which are specifically incorporated into this specification by reference with one or more of the bone bolts described herein.

Figure 2:
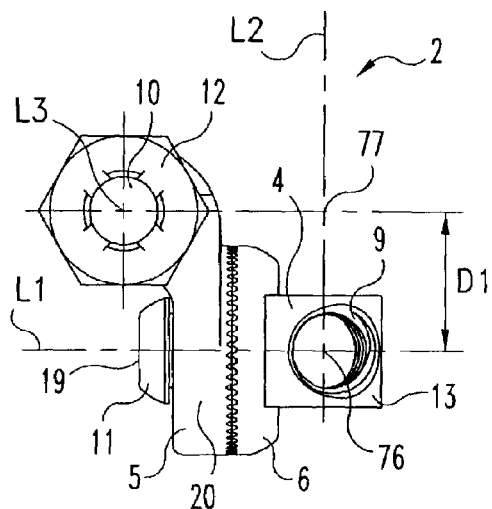
FIGS. 2-4 are respectively top, side, and cross-sectional views of a clamp that may be used in one embodiment of the present invention.
Figure 3:
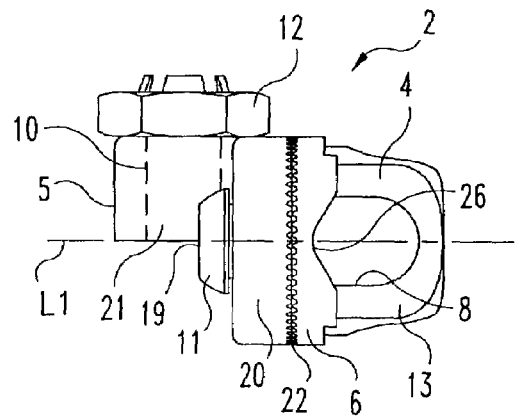
Figure 4:
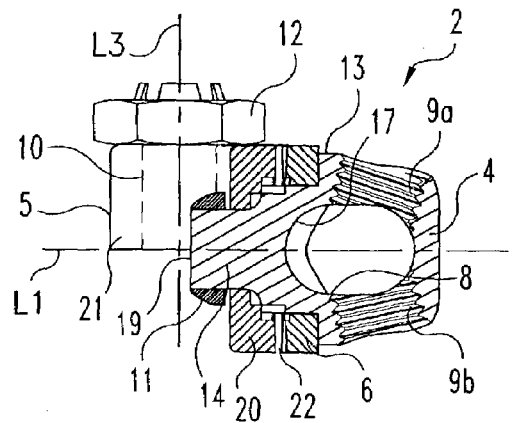
Figure 5:
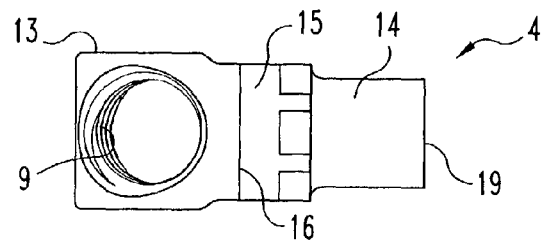
FIGS. 5-8 are respectively, top, side, end, and cross-sectional views of a clamp bolt that may be used in one embodiment of the present invention.
Figure 6:
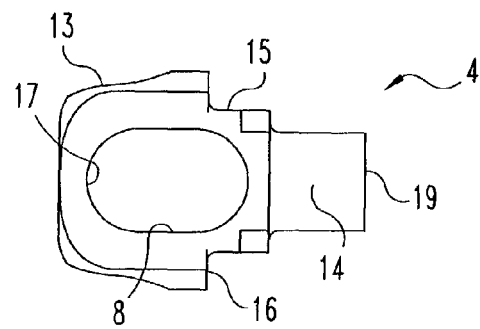
Figure 7:
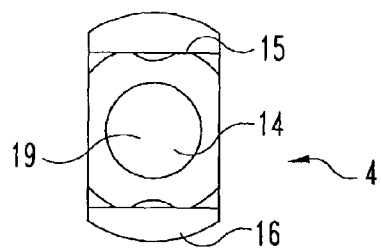
Figure 8:
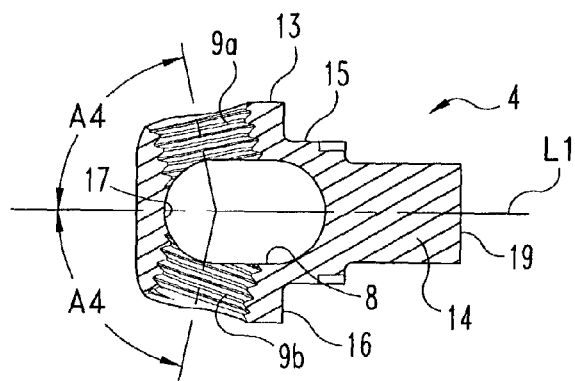

Clamp 2 is depicted in FIGS. 2-4, less set screw 7, which has been removed for clarity along with rod 3 and bone bolt 1. The clamp is used by placing spinal rod 3 through aperture 8. The connector portion 44 of bone bolt 1 is then threaded through bore 10 and nut 12 of clamp 2 as the surgeon desires. Arm 5 and the variable angle ridges 31 on the rod interface washer 6 are then interlocked with the variable angle ridges 23 on arm 5, and the assembly is tightened by threading set screw 7 into either of the threaded openings 9, (or by optionally turning stop 11 around connector portion 44 as described in an alternative embodiment). Upon entering aperture 8, set screw 7 contacts the spinal rod and forces the spinal rod toward interface washer 6. The spinal rod then contacts rod interface washer 6, and engages groove 26. As one continues turning set screw 7, rod interface washer 6 presses flange portion 20 of arm 5 against stop 11. The variable angle surfaces, item 23 on arm 5 and item 31 on rod interface washer 6, firmly engage each other and prevent rod interface washer 6 from rotating in relation to arm 5, which further locks arm 5 in relation to clamp bolt 4 because rod interface washer 6 cannot rotate in relation to clamp bolt 4. Adjustments can be made by loosening set screw 5 then re-tightening the set screw when the preferred position has been located. The surgeon can adjust the longitudinal position of bone bolt 1 by rotating nut 12 as the surgeon desires. The set screws 7 shown in FIG. 1 are of a type that shear at 75 when the appropriate amount of torque has been placed on set screw 7. Such set screws are now well-known in this art.

Referring to FIGS. 1 & 2, one may note some additional features of this invention by noting the locations of various longitudinal axes. L1 is the longitudinal axis of a portion of clamp 2. L2 is the longitudinal axis of rod 3, and L3 is the longitudinal axis of both connector portion 44 of bolt 1 and bore 10 in arm 5. In this regard, one may not that L3 is offset from L1 a distance D1. In other words, clamp 2 will contact rod 3 at 76, and L3 or bore 10 is spaced from 76 a distance D1 along rod 3. In many circumstances involving patient anatomy, distance D1 may help the surgeon place clamp 2 and/or bone bolt 1 in a manner that avoids interfering with the patient's anatomy, such as the facet joints of the spine.

A bone bolt 101 according to another embodiment of the present invention is shown in FIGS. 29-37. Bone bolt 101 is usable in the spinal implant system of FIG. 1 in addition to bone bolt 1 and/or as a replacement for bone bolt 1. Preferably, bone bolt 101 is used in a reduction assembly such as those disclosed in U.S. Pat. No. 6,248,107, issued Jun. 19, 2001, which is incorporated herein by reference. The use of an "N" hundred prefix with an element number (NXX) refers to an element that is the same as the non-prefixed element number (XX), except for the changes or modifications shown or described hereafter.

Bone bolt 101 includes a connector portion 144 that is pivotally coupled to a mounting portion 142 by a pin 152. In one embodiment, connector portion 144 is pivotal about pin 152 in an asymmetric manner as indicated by arc A105. In the embodiment shown, arc A105 extends from a first position at the approximate alignment of axes L3 and L4 to a second position in which axis L3 is rotated about 60 degrees from axis L4. However, the present invention also includes those embodiments in which axis L3 describes an arc that is approximately symmetric about axis L4, and also those embodiments in which the arc traversed by connector portion 144 is not symmetric about axis L4, but in which portions of the arc lie on both sides of axis L4.

Figure 30:
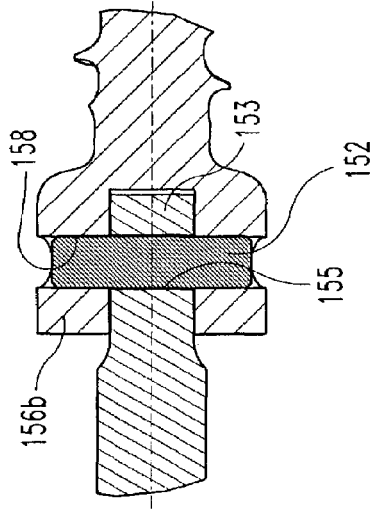
FIG. 30 is a cross sectional view of a portion of the bone bolt of FIG. 29 as taken along line 30-30 of FIG. 29.
Figure 33:
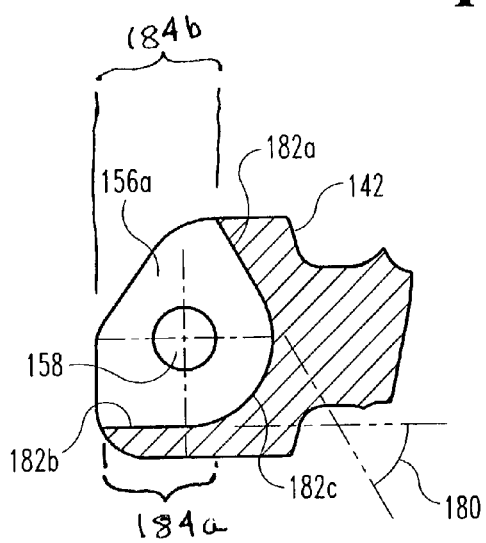
FIG. 33 is a cross sectional view of a portion of the apparatus of FIG. 32 as taken along lines 33-33 of FIG. 32.
Figure 34:
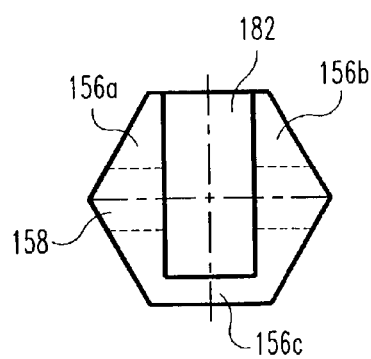
FIG. 34 is an end elevational view of the apparatus of FIG. 31.

Referring to FIGS. 31-34, a bone screw or mounting portion 142 is shown. At the end of mounting portion 142 opposite of tapered tip 146 are a pair of generally parallel ears 156a and 156b. Ears 156a and 156b are connected together by a central portion 156c located along one side of the hex-head of mounting portion 144, as best seen in FIG. 34. Portions 156a, 156b, and 156c define a central slot 182 which receives an ear 153 of connector portion 144 (as best seen in FIG. 30). Referring again to FIGS. 31-34, in one embodiment of the present invention, slot 182 includes interior walls 182a and 182b joined by a semi-circular wall 182c. In one embodiment, interior walls 182a and 182b define an interior angle 180 of about 60 degrees. Ears 156a and 156b also define an aperture 158 which receives pin 152 of bone bolt 101 (as best seen in FIG. 30).

Figure 35:
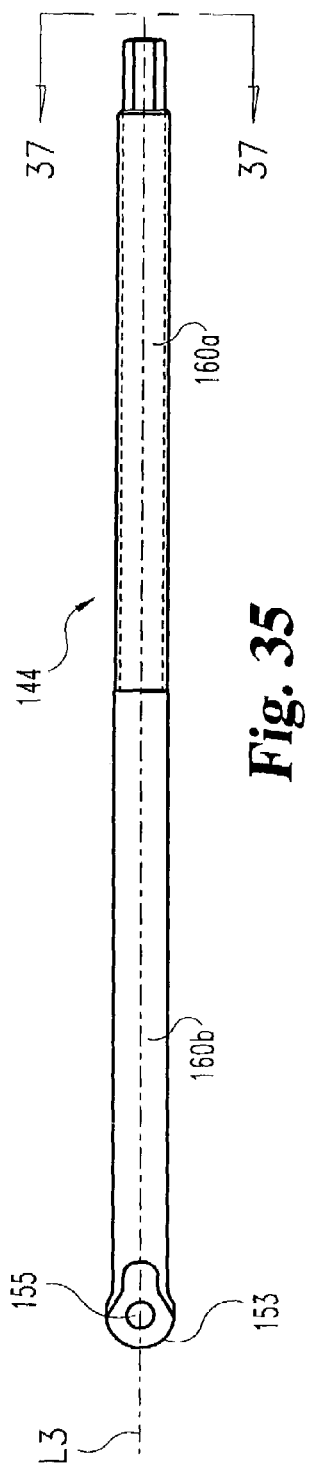
FIG. 35 is a side elevational view of the connector portion of the bone bolt of FIG. 29.
Figure 36:
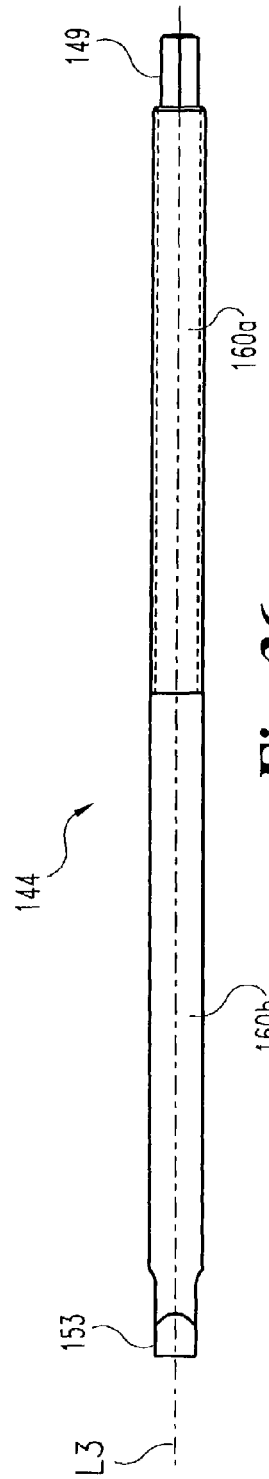
FIG. 36 is a top plan view of the apparatus of FIG. 35.
Figure 37:
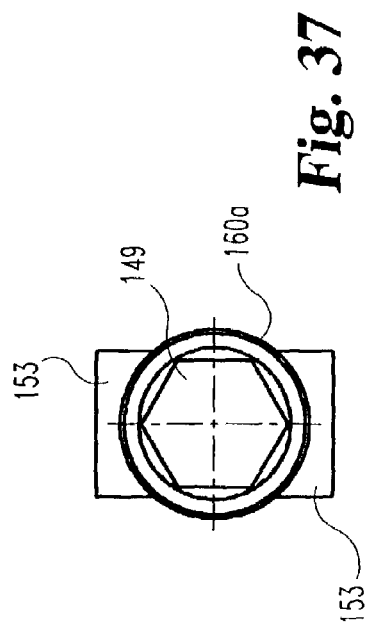
FIG. 37 is an end elevational view of the apparatus of FIG. 35 as taken along lines 37-37 of FIG. 35.

FIGS. 35-37 depict a connector portion 144 according to one embodiment of the present invention. Rod or connector portion 144 includes a threaded portion 160a which preferably includes machine threads for coupling to nut 12 (referring to FIG. 1). In some embodiments of the present invention, connector portion 144 threadably couples to a nut which does not includes the rim and collar shown with nut 12.

Referring again to FIGS. 35-37, some embodiments of the present invention include a clean, unthreaded portion 160b along rod 144 between threaded portion 160a and ear 153. In those embodiments in which bone bolt 101 is utilized in the assembly of U.S. Pat. No. 6,248,107 as a replacement for the reduction bolt, a set screw provides securement of the clamp anywhere along the length of unthreaded portion 160b. The smooth shank region 160b permits infinite medial-lateral adjustment and infinite dorsal adjustment of the clamp within the range of the smooth shank 160b. Commercial embodiments of the apparatus disclosed herein are sold under the trademark TSRH-3D and are available from Medtronic Sofamor Danek, of Memphis, Tenn., U.S.A.

Ear 153 is adapted and configured to permit constrained pivoting within slot 182 of mounting portion 142. In one embodiment, ear 153 includes a radiused portion adapted and configured to fit within radius 182c of slot 182. Ear 153 further includes an aperture 155 which aligns with apertures 158 and receives pin 152, as best seen in FIG. 30. In some embodiments, connector portion 144 includes a hex-shaped end 149 opposite of ear 153. Hex-end 149 can be used to apply a tightening or loosening torque to bone bolt 101.

Referring again to FIG. 29, the flattened parallel sides of ear 153 are received between spaced apart, parallel ears 156a and 156b of mounting portion 142. A pin 152 received within apertures 155 and 158 pivotally couples connector portion 144 to mounting portion 142. The present invention contemplates pin 152 being received in an interference fit in any one of ears 156a, and 156b, or 153. Further, pin 152 can be coupled to any of these ears by staking or other methods.

Figure 29:
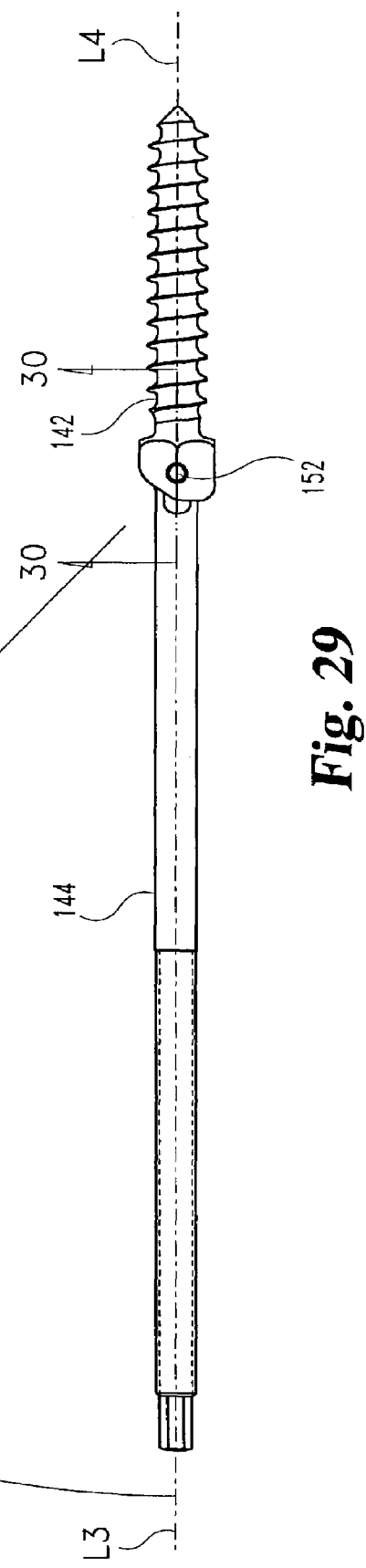
FIG. 29 is a side elevational view of a bone bolt according to another embodiment of the present invention.
Figure 31:
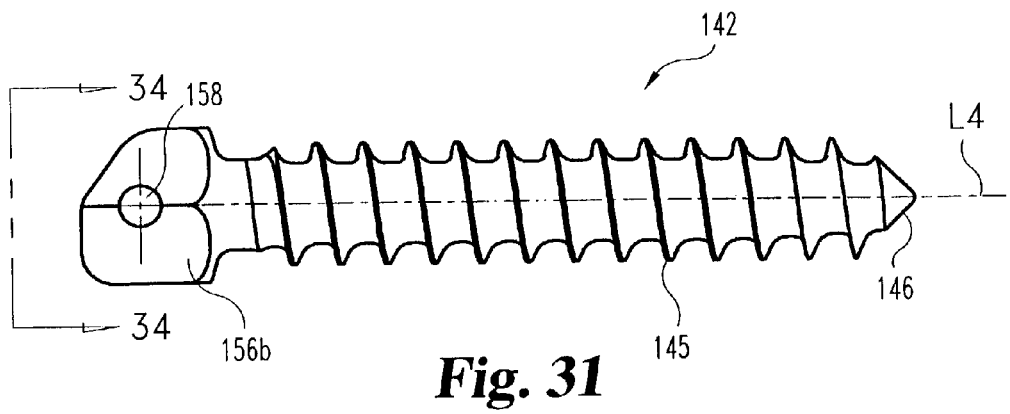
FIG. 31 is a side elevational view of a mounting portion of the bone bolt of FIG. 29.
Figure 32:
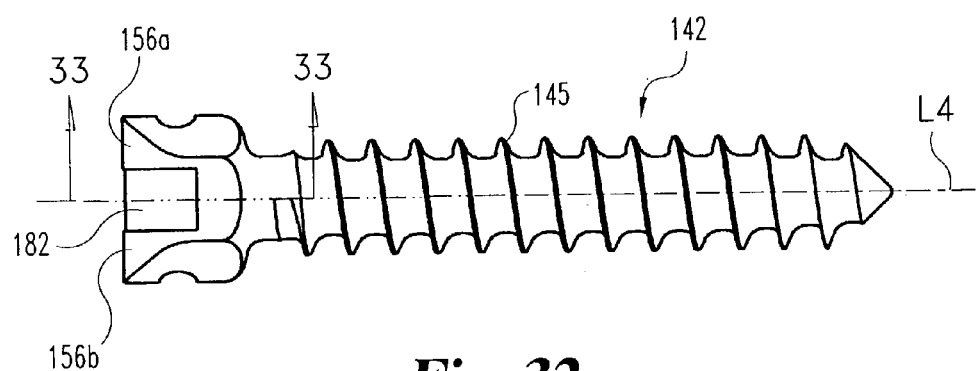
FIG. 32 is a top plan view of the mounting portion of the bone bolt of FIG. 29.

Ear 153 and channel 182 preferably are adapted and configured to permit constrained-arc asymmetric pivoting of connector portion 144 about mounting portion 142. As seen in FIG. 29, in one embodiment of the present invention connector portion 144 of bone bolt 101 is pivotal about an arc A105 which extends from the approximate alignment of axes L3 and L4 in an arc that extends toward the open side of slot 182. However, the present invention also contemplates those embodiments in which a portion of the described arc is located on either side of the alignment of axes L3 and L4. Preferably, arc A105 is less than about 90 degrees.

Referring to FIG. 33, in one embodiment of the present invention the asymmetric motion is a result of the co-action of the asymmetric slot 182 with ear 153 of connector portion 144. Slot 182 includes a lateral wall 184a that is generally opposite of an open portion 184b of slot 182. Connector portion 144 can pivot toward inner wall 182 until a portion of wall 182 contacts a portion of connector 144. Pivotal motion is constrained in the other direction by the co-action of inner wall 182b with the other side of ear 153 and connector 144.

Although what has been shown and described is a bone screw or mounting portion 142 with slot 182 that receives an ear 153 of rod or connector portion 144, the present invention also contemplates those embodiments in which the slot is part of the connector portion, and in which the mounting portion includes an ear received within the slot. Further, although what has been shown and described is an ear 153 that is received within a slot formed by ears 156a and 156b, the present invention also contemplates those embodiments in which an end of either the mounting portion or connector portion defines a receptacle, and an end of the other of the mounting portion or connecting portion defines a projection. Either the mounting portion or the connector portion can have the receptacle. In these embodiments, the receptacle and projection are adapted and configured to coact to permit pivotal movement of the connector portion relative to the mounting portion. Further, in some embodiments the movement is constrained to be less than 90 degrees, and in other embodiments is constrained to be asymmetric about axis L4 or axis L3.

The present invention contemplates various types of pivotal motion. Although what has been shown and described is pivotal motion that is generally perpendicular to axis L4 or axis L3, the present invention also contemplates those embodiments in which the pivotal motion includes a first directional component that is perpendicular to axis L3 or L4, and a second directional component that is parallel to axis L3 or L4. For example, these alternate embodiments can include a pivoting axis that is non-perpendicular to axis L4 (for example, such as by alignment of apertures 158 to be non-perpendicular to axis L4, as would be seen in a view similar to that of FIG. 32). In these embodiments, the pivotal motion of the connector portion relative to the mounting portion includes a rotational component parallel to axis L4, such that pivotal motion of the connector portion would create some pivotal motion about axis L4.

Referring to FIG. 38, a bone bolt 201 is shown according to another embodiment of the present invention. Bone bolt 201 is the same as bone bolt 101, except with regards to connector portion 244. Connector portion 244 includes a clean, unthreaded section, 260*b* which terminates at one end in an internal hex head 249. In such embodiments of the present invention, there is no need for coupling to a nut such as nut 12. Instead, securement to bone bolt 201 is accomplished by use of a set screw in the clamp, as shown in U.S. Pat. No. 6,248,107.

Although various embodiments of bone bolts have been shown and described, the present invention also contemplates those embodiments in which connector portions 144 and 244 are generally threaded, and have little, if any, unthreaded portions. Further, the present invention contemplates various lengths of mounting portions and connector portions. For example, the connector portion 244 shown in FIG. 38 in one embodiment is less than about one-half of the length shown in FIG. 38.

While the invention has been illustrated and described in detail, this is to be considered as illustrative and not restrictive of the patent rights. The reader should understand that only the preferred embodiments have been presented and all changes and modifications that come within the spirit of the invention are included if the following claims or the legal equivalent of these claims describes them.

What is claimed is:

1. A spinal orthopedic bolt apparatus comprising:

a monolithic bone screw having two parallel ears, said bone screw ears defining a central slot open to an upper part of said bone screw, said slot having a curved lower surface generally facing the opening of the slot and extending between said bone screw ears, said bone screw ears each including an aperture, said apertures being collinear;

a monolithic rod having a smooth portion, a first end and a second end, said first end having a hexagonal print for connection to a tool for providing torque to said rod, said second end including a rounded ear integral with said smooth portion, said rounded ear further including two opposing flat surfaces and a central hole extending between said surfaces, said rounded ear of said rod being inserted into said slot so that said flat surfaces are adjacent said bone screw ears, said central hole is substantially collinear with said apertures of said bone screw, and said smooth portion extends above said bone screw ears; and a pin inserted in said apertures of said bone screw ears and crossing said slot, wherein said rod allows a clamp to contact said smooth portion anywhere along the length of said smooth portion, permitting infinite medial-lateral adjustment and infinite dorsal adjustment of the clamp within the range of said smooth portion.

2. The apparatus of claim 1, wherein said rounded ear has a radius, and said curved lower surface has a radius, and said radii are substantially equal.

3. The apparatus of claim 1, wherein said print is an external print.

4. The apparatus of claim 1, wherein said rod includes a machine threaded portion between said print and said smooth portion.

5. The apparatus of claim 4, wherein the length of said machine threaded portion is substantially the same as the length of said smooth portion.

6. The apparatus of claim 1, wherein said rod can occupy a range of positions with respect to said bone screw by pivoting around said pin, and said range of positions is less than a half-circle.

7. The apparatus of claim 1, wherein said rod has a first longitudinal axis, and said bone screw has a shaft with a second longitudinal axis, and said rod and said bone screw have a first relative position in which said axes are collinear, and wherein said rod can pivot with respect to said bone screw around said pin to other relative positions in which said axes are noncollinear, and the included angle between any of said other relative positions and said first relative position is less than 90 degrees.

8. The apparatus of claim 1, wherein said ears of said bone screw form part of a hexagonal-shaped head of said bone screw.

9. The apparatus of claim 1, said apparatus being connected to a spinal support rod.

* * * * *